US007569149B2

(12) United States Patent
Koch et al.

(10) Patent No.: US 7,569,149 B2
(45) Date of Patent: Aug. 4, 2009

(54) IONIC LIQUIDS AS SOLVENTS IN HEADSPACE GAS CHROMATOGRAPHY

(75) Inventors: Peter Koch, Freiburg (DE); Ernst Küsters, Eschbach (DE)

(73) Assignee: Novartis AG, Basel (CH)

( * ) Notice: Subject to any disclaimer, the term of this patent is extended or adjusted under 35 U.S.C. 154(b) by 348 days.

(21) Appl. No.: 10/521,638

(22) PCT Filed: Jul. 28, 2003

(86) PCT No.: PCT/EP03/08315

§ 371 (c)(1),
(2), (4) Date: Jan. 19, 2005

(87) PCT Pub. No.: WO2004/013612

PCT Pub. Date: Feb. 12, 2004

(65) Prior Publication Data

US 2005/0205493 A1   Sep. 22, 2005

(30) Foreign Application Priority Data

Jul. 29, 2002   (GB)   ................... 0217499.3

(51) Int. Cl.
*B01D 15/12* (2006.01)
*G01N 30/02* (2006.01)
*G01N 30/12* (2006.01)
*B01D 15/08* (2006.01)

(52) U.S. Cl. .............. 210/656; 73/19.02; 73/23.35; 73/61.52; 422/70; 422/89; 436/161

(58) Field of Classification Search ............... None
See application file for complete search history.

(56) References Cited

U.S. PATENT DOCUMENTS

| 5,827,944 A | 10/1998 | Nickerson |
| 6,369,243 B1 | 4/2002 | MacMillan et al. |
| 6,380,420 B1 | 4/2002 | Schinski et al. |
| 2001/0031875 A1 | 10/2001 | Kitazume |
| 2002/0063240 A1 | 5/2002 | Munson et al. |

FOREIGN PATENT DOCUMENTS

| JP | 4215062 A | * | 5/1992 |
| JP | 04 215062 | | 8/1992 |

OTHER PUBLICATIONS

Armstrong et al., "Examination of ionic liquids and their interactions with molecules, when used as stationary phases in gas chromatography", Anal. Chem. 1999, 71, 3873-3876.*
Jiang Peng, et al, "Effect of ionic strength on Henry's Constants of volatile organic compounds", Chemosphere, vol. 36, No. 13, pp. 2731-2740, 1998.*
Kolb et al, "Analysis of water in liquid and solid samples by headspace gas chromatography", Fresenius J. Anal. Chem., (1990) 336, 297-302.*

(Continued)

*Primary Examiner*—Krishnan S Menon
(74) *Attorney, Agent, or Firm*—Sandra Shim; John W. Kung

(57) ABSTRACT

A method of using an ionic liquid as solvent in headspace gas chromatography.

3 Claims, 4 Drawing Sheets

OTHER PUBLICATIONS

Comberbach et al, "Automatic online fermentation headspace gas analysis using a comnputer controoled gas chromatograph", Biotechnology and bioengineering, vol. XXV, pp. 2503-2518 (1983).*

Banat, et al , "Experimental study of salt effect in vapor/liquid equilibria using headspace gas chromatography", Chem Engg Tech., 22 (1999) 9.*

Nagai Yumi, Science Links Japan: Analysis of Residual solvents in pharmaceuticals by headspace gas chromatography, Shimadzu review, (2002).*

Kumar, et al. "Headspace gas chromatography method for the analysis of volatile impurities in hormone replacement trans-dermal patch", Journal of Chromatography A, 859 (1999) 113-118.*

Russo: "Static headspace gas chromatography of residual solvents in pharmaceutical products", Chromatographia vol. 39, No. 11/12, Dec. 1994.*

Jian Peng et al., "Effect Of Ionic Strength On Henry's Constants Of Volatile Organic Compounds", Chemosphere, vol. 36, No. 13, pp. 2731-2740, (Jun. 1998).

Banat F A et al., "Experimental Study Of The Salt Effect In Vapor/Liquid Equilibria Using Headspace Gas Chromatography", Chemical Engineering and Technology, vol. 22, No. 9, pp. 761-765, (1999).

Patent Abstracts of Japan, vol. 16, No. 562 (P-1456), (Dec. 1992).

Comberbach D M et al., "Automatic On-Line Fermentation Headspace Gas Analysis Using A Computer-Controlled Gas Chromatograph", Biotechnology and Bioengineering. Including Symposium Biotechnology In Energy Production and Conservation, John Wiley and Sons, New York, vol. 25, No. 11, pp. 2503-2518, (1983).

Kolb B et al., "Analysis Of Water In Liquid And Solid Samples By Headspace Gas Chromatography Part II: Insoluble Sold Samples By The Suspension Approach", Fresenius Journal of Analytical Chemistry, vol. 336, No. 4, pp. 297-302, (1990).

Wasserscheid, Peter, et al: "Ionic Liquids in Synthesis", Wiley-VCH (2003), pages 1-6.

Cooper, E.R., et al: "Ionic liquids and eutectic mixtures as solvent and template in synthesis of zeolite analogues", Nature, vol. 430, Aug. 2004, pp. 1012-1016.

* cited by examiner

IONIC LIQUIDS AS SOLVENTS IN HEADSPACE GAS CHROMATOGRAPHY

The present invention provides a method of using an ionic liquid as solvents in headspace gas chromatography.

The purity of a compound may affect many physical and chemical properties of the compound, for example, the electrical conductivity, luminescence, capacity for polymerization, and stability. Even impurities present in very low amounts, for example, $10^{-2}$ to $10^{-9}$, may deleteriously affect the properties of a compound or the analysis of the compound, and thus, prevent a compound from being used in its intended field. This is especially true in the pharmaceutical industry where impurities in a drug compound may decrease bioavailability of the drug, and prevent the Food and Drug Administration from either approving the drug, or approving a process to prepare the drug.

Volatile constituents of samples have been determined by gas chromatography (GC) advantageously for the following reasons: (i) GC provides in a single analysis information about many impurities, not just a single one, particularly because it gives very sharp separations, which allows one to analyze for impurities that differ only slightly in properties, such as isomers; (ii) sensitive detectors allow one to detect impurities at very low concentrations; (iii) headspace gas chromatography can be combined with spectroscopic instruments for identification of separated compounds; and (iv) accumulation techniques can be used independently to reduce further the minimum detectable concentration.

Other methods of gas analysis exist, such as mass spectrometry, IR spectroscopy and UV spectroscopy, for the determination of compounds in their vapor state in the presence of liquids and solids. However, these methods are often insufficiently sensitive, and when several materials are present in the vapor phase, they give inextricably complex results, since only the sum of the components can be measured.

Headspace gas chromatography (HSGC) generally consists of a static or dynamic headspace gas sampling device, which may be manually operated or automated, and a gas chromatograph. The headspace sampling device variants allow for selectively volatilizing the volatile components of a test sample. A representative fraction or the total amount of the volatile components is carried into the chromatographic column mounted in the oven of a gas chromatograph. Several variants of technical realizations are commercially available or can be handcrafted. Static headspace sampling devices apply, for example, balanced pressure injection, loop-injection or syringe injection. In a first step, dynamic headspace sampling device usually, but not exclusively, preconcentrate a representative fraction or the total amount of the volatile components of the test sample in a trap. In the second step, a representative fraction or the total amount of the preconcentrated volatile components of the test sample is then carried from the trap into the chromatographic column mounted in the oven of a gas chromatograph. A flow of carrier gas carries the volatile components through the chromatographic column where they are separated. The separated components enter a detector, which determines the concentration or mass flow of the components in the carrier gas.

Ionic liquids have been used as solvents for a number of reactions, for example, Friedel-Crafts reactions (Adams, C. J., et al., *Chemistry Communications,* 1998, pgs. 2097-2098; isomerisation of fatty acid derivatives (WO 98/07679, and U.S. Pat. No. 6,255,504); dimerization, co-dimerization and oligomerization of olefins (U.S. Pat. Nos. 5,550,306, and 5,104,840); Diels-Alder reactions (Earle, M. J., et al., *Green Chemistry,* 1999, vol. 1, pgs. 23-25); and hydrogenation reactions (Fisher, T., et al. Tetrahedron Letters, 1999, vol. 40, pgs. 793-794).

Disadvantages associated with using conventional solvents in headspace gas chromatography are (i) high vapor pressure which causes broad solvent peaks in the chromatogram; (ii) limited temperature range of application; and (iii) carry over from consecutive injections in the gas chromatograph. Therefore, it would be desirable to have a method that allows for the detection, and/or quantification, and/or identification of volatile components in a test sample without the disadvantages arising from conventional solvents.

The invention provides the use of an ionic liquid as solvent in headspace gas chromatography.

In another aspect the invention provides the use of an ionic liquid as solvent in headspace gas chromatography wherein said method comprises dissolving or dispersing a sample in at least one ionic liquid and volatilizing the volatile components of the sample.

In a further aspect the invention provides a method to detect volatile components in a sample by headspace gas chromatography, wherein said method comprises dissolving or dispersing a sample in at least one ionic liquid and volatilizing the volatile components of the sample. For example, the ionic liquid has essentially no vapor pressure.

According to another aspect the invention provides a method to quantify and/or identify volatile components in a sample by headspace gas chromatography, wherein said method comprises dissolving or dispersing a sample in at least one ionic liquid and volatilizing the volatile components of the sample.

In another aspect the invention provides the use of an ionic liquid as solvent in headspace gas chromatography for the detection, e.g. quantification and/or identification, of impurities in a sample, e.g. in a pharmaceutical compound.

Hereinafter follows a brief description of the drawings.

Figure 1:
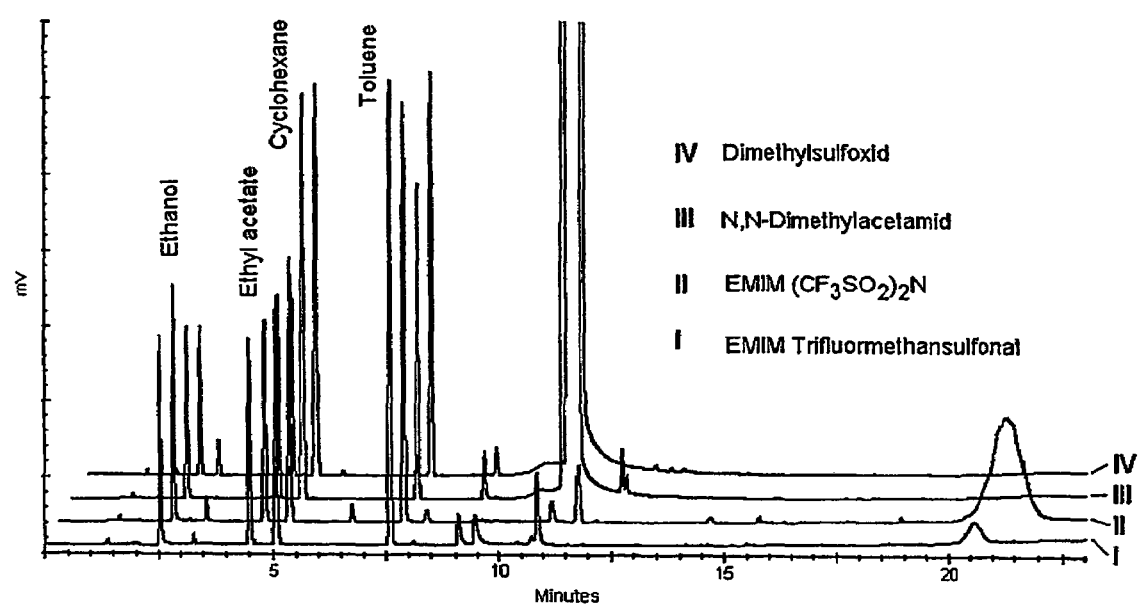
FIG. 1 is a headspace gas chromatogram showing residual solvents in 1-ethyl-3-methyl-imidazolium trifluoromethanesulfonate (I), 1-ethyl-3-methyl-imidazolium bis-(trifluoromethanesulfonyl)-imidate (II), N,N-dimethylacetamide (III) and dimethylsulfoxide (IV).

The method of the invention uses ionic liquids as solvents in headspace gas chromatography to detect volatile components in a sample, wherein said method comprises dissolving or dispersing a sample in at least one ionic liquid and volatilizing the volatile components of the sample. In another embodiment of the invention, the method of the invention is used to quantify and/or identify volatile components in a sample by headspace gas chromatography, wherein said method comprises dissolving or dispersing a sample in at least one ionic liquid and volatilizing the volatile components of the sample. The volatile components of a sample can be analyzed by the method of the invention.

As used herein, "gas chromatography or "gas chromatographic" includes gas-liquid chromatography and gas-solid chromatography. As used herein, "headspace" includes static headspace techniques and dynamic headspace techniques. Headspace gas chromatography and gas chromatography are known to those skilled in the art of analytical chemistry.

As used herein, "samples" includes gas, liquid, and solid materials. A combinabon of materials may also be used. Examples of samples which may be used in the method of the invention include, but are not limited to, liquid samples, such as drinking water, beverages, vegetable oils, mineral oils, etc; samples containing a liquid and a solid, such as blood, milk, sewage, polymer dispersions, etc; solid materials which give homogenous solutions, such as soluble polymers, inorganic salts, etc; insoluble solid samples, such as high molecular weight olefins, foodstuffs, fruits, tobacco, spices, etc; air, dioxins, PCB's, and pharmaceutical compounds.

Ionic liquids are characterized by a positively charged cation and a negatively charged anion. Generally, any molten salt or mixture of molten salts is considered an ionic liquid. Ionic liquids typically have essentially no vapor pressure, good heat transfer characteristics, are stable over a wide temperature range, and are capable of dissolving a wide range of material in high concentrations. As used herein, "essentially no vapor pressure" means that the ionic liquid exhibits a vapor pressure of less than about 1 mm/Hg at 25° C., for example less than about 0.1 mm/Hg at 25° C.

With respect to the type of ionic liquid, a wide variety of possibilities exist. However, the preferred ionic liquids are liquid at relatively low temperatures, for example, below the melting point of the compound or sample to be analyzed. For example, the ionic liquid has a melting point of less than 250° C., further example less than 100° C. For example, the ionic liquid has a melting point of less than 30° C. or is a liquid at room temperature.

With regard to viscosity of the ionic liquid, it is important that the viscosity of the ionic liquid is not too high to prevent a homogeneous solution or dispersion of a compound or sample in an ionic liquid. For example, the ionic liquid has a viscosity of less than 500 centipoise (cP), further example, less than 300 cP, or less than 100 cP, as determined at 25° C.

In another aspect of the invention the ionic liquid is stable over a wide temperature range. Such a ionic liquid may be useful for the temperature programs used in headspace gas chromatography. The thermal stability of the ionic liquid may be from 150° C. to 400° C., for example from 200° C. to 300° C.

In a further aspect the invention provides a method according the invention wherein the ionic liquid has a melting point as described herein above, e.g. of less than 250° C., a vapor pressure as described herein above, e.g. less than about 1 mm/Hg at 25° C. and thermal stability as described herein above, e.g. is from 150° C. to 400° C.

The cation present in the ionic liquid can be a single species or a plurality of different species. Both of these embodiments are intended to be embraced, unless otherwise specified, by the use of the singular expression "cation." The cations of the ionic liquid include organic and inorganic cations. Examples of cations include quaternary nitrogen-containing cations, phosphonium cations, and sulfonium cations.

The quaternary nitrogen-containing cations are not particularly limited and embrace cyclic, aliphatic, and aromatic quaternary nitrogen-containing cations. For example, the quaternary nitrogen-containing cation is an n-alkyl pyridinium, a dialkyl imidazolium, or an alkylammonium of the formula $R'_{4-X}NH_X$ wherein X is 0-3 and each R' is independently an alkyl group having 1 to 18 carbon atoms. It is believed that unsymmetrical cations can provide for lower melting temperatures. The phosphonium cations are not particularly limited and embrace cyclic, aliphatic, and aromatic phosphonium cations. For example, the phosphonium cations include those of the formula $R''_{4-X}PH_X$ wherein X is 0-3, and each R" is an alkyl or aryl group such as an alkyl group having 1 to 18 carbon atoms or a phenyl group. The sulfonium cations are not particularly limited and embrace cyclic, aliphatic, and aromatic sulfonium cations. For example, the sulfonium cations include those of the formula $R'''_{3-X}SH_X$ wherein X is 0-2 and each R''' is an alkyl or aryl group such as an alkyl group having 1 to 18 carbon atoms or a phenyl group. The following cations may be used: 1-hexylpyridinium, ammonium, imidazolium, 1-ethyl-3-methylimidazolium, 1-butyl-3-methylimidazolium, phosphonium, and N-butylpyridinium.

The anion used in the ionic liquid is not particularly limited and includes organic and inorganic anions. Generally the anion is derived from an acid, especially a Lewis acid. The anions are typically metal halides as described in more detail below, boron or phosphorus fluorides, alkylsulfonates including fluorinated alkyl sulfonates such as nonafluorobutanesulfonate, and carboxylic acid anions such as trifluoroacetate and heptafluorobutanoate. The anion is for example $Cl^-$, $Br^-$, $NO_2^-$, $NO_3^-$, $AlCl_4^-$, $BF_4^-$, $PF_6^-$, $CF_3COO^-$, $CF_3SO_3^-$, $(CF_3SO_2)_2N^-$, $OAc^-$, $CuCl_3^-$, $GaBr_4^-$, $GaCl_4^-$, and $SbF_6^-$.

Examples of ionic liquids include, but are not limited to, imidazolium salts, pyridinium salts, ammonium salts, phosphonium salts, and sulphonium salts. For example imidazolium salts have formula (I)

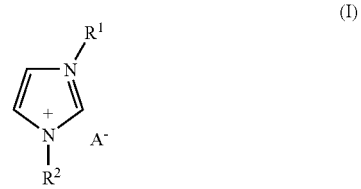

wherein $R^1$ and $R^2$ are independently selected from the group consisting of a $C_1$-$C_{18}$ aliphatic group and a $C_4$-$C_{18}$ aromatic group; and $A^-$ is an anion.

For example ammonium salts have formula (II)

wherein $R^3$, $R^4$, $R^5$ and $R^6$ are independently selected from the group consisting of a $C_1$-$C_{18}$ aliphatic group and a $C_4$-$C_{18}$ aromatic group; and $A^-$ is an anion. For example, $R^3$, $R^4$, $R^5$ and $R^6$ are independently selected from the group consisting of ethyl, propyl and butyl.

For example phosphonium salts have formula (III)

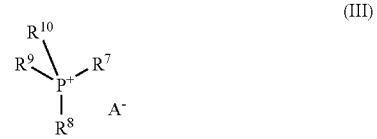

wherein $R^7$, $R^8$, $R^9$, and $R^{10}$ are independently selected from the group consisting of a $C_1$-$C_{18}$ aliphatic group and a $C_4$-$C_{18}$ aromatic group; and A⁻ is an anion. For example, $R^7$, $R^8$, $R^9$, and $R^{10}$ are independently selected from the group consisting of ethyl and butyl.

For example pyridinium salts have formula (IV)

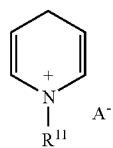

(IV)

wherein $R^{11}$ is selected from the group consisting of a $C_1$-$C_{18}$ aliphatic group and a $C_4$-$C_{18}$ aromatic group; and A⁻ is an anion. For example $R^{11}$ is ethyl or butyl.

Specific examples of ionic liquids include, but are not limited to, 1-butyl-3-methylimidazolium hexafluorophosphate, 1-hexyl-3-methylimidazolium hexafluorophosphate, 1-octyl-3-methylimidazolium hexafluorophosphate, 1-decyl-3-methylimidazolium hexafluorophosphate, 1-dodecyl-3-methylimidazolium hexafluorophosphate, 1-ethyl-3-methylimidazolium bis(trifluoromethylsulphonyl)amide, 1-hexyl-3-methylimidazolium bis(trifluoromethylsulphonyl)amide, 1-hexylpyridinium tetrafluoroborate, 1-octylpyridinium tetrafluoroborate, 1-butyl-3-methylimidazolium tetrafluoroborate, 1-methy-3-ethyl imidazolium chloride, 1-ethyl-3-butyl imidazolium chloride, 1-methy-3-butyl imidazolium chloride, 1-methy-3-butyl imidazolium bromide, 1-methy-3-propyl imidazolium chloride, 1-methy-3-hexyl imidazolium chloride, 1-methy-3-octyl imidazolium chloride, 1-methy-3-decyl imidazolium chloride, 1-methy-3-dodecyl imidazolium chloride, 1-methy-3-hexadecyl imidazolium chloride, 1-methy-3-octadecyl imidazolium chloride, 1-methy-3-octadecyl imidazolium chloride, ethyl pyridinium bromide, ethyl pyridinium chloride, ethylene pyridinium dibromide, ethylene pyridinium dichloride, butyl pyridinium chloride, and benzyl pyridinium bromide.

For example, ionic liquids are 1-octyl-3-methyl-imidazolium hexafluorophosphate, 1-hexyl-3-methy-imidazolium hexafluorophosphate, 1-butyl-3-methyl-imidazolium hexafluorophosphate, 1-butyl-3-methyl-imidazolium tetrafluoroborate, 1-butyl-3-methyl-imidazolium trifluoromethanesulfonate, 1-ethyl-3-methyl-imidazolium trifluoromethanesulfonate, and 1-ethyl-3-methyl-imidazolium bis-(trifluoromethylsulfonyl)-amide. In one aspect of the invention, the ionic liquid is 1-octyl-3-methyl-imidazolium hexafluorophosphate or 1-hexyl-3-methy-imidazolium hexafluorophosphate.

A mixture of ionic liquids, including binary ionic liquids, may also be used. The ionic liquids may be prepared by any of the methods described in the art.

The sample or compound to be analyzed by headspace gas chromatography is dissolved or dispersed, for example dissolved, in the ionic liquid. The amount of ionic liquid is not particularly limited. For example, about 1 to about 100 mg of a sample or compound to be analyzed is dissolved or dispersed in about 0.1 to about 5 ml of ionic liquid.

The advantages of the method of the present invention include that: (i) ionic liquids have essentially no vapor pressure, thus, no interfering solvent peaks are generated by the ionic liquids; (ii) less overpressure is generated inside a sample vial containing an ionic liquid as compared to a conventional solvent, which reduces seal failure and leakage of the vial; (iii) ionic liquids have high thermal stability which allows the application range of headspace gas chromatograph to be expanded; (iv) the high thermal stability of ionic liquids allows the detection limit of headspace gas chromatograph to be expanded; and (v) headspace gas chromatography allows for detection of volatile impurities in ionic liquids; and (vi) ionic liquids may bed analyzed by headspace gas chromatography.

The following non-limiting examples illustrate further aspects of the method of the invention.

EXAMPLES

Headspace Gas Chromatography Analysis of Volatile Solvents.

Example 1

Four vials are prepared which each contain 39.5 μg ethanol, 45 μg ethyl acetate, 39.0 μg cyclohexane, and 43.5 μg toluene, which are dissolved in 0.1 ml of either one of the following ionic liquids: 1-ethyl-3-methyl-imidazolium trifluoromethanesulfonate or 1-ethyl-3-methyl-imidazolium bis-(trifluoromethanesulfonyl)-imidate, or one of the following conventional solvents: dimethylsulfoxide or N,N-dimethylacetamide.

The chromatograms are obtained using Agilent Equipment (Headspace Autosampler 7694, a Gas chromatograph 5890 equipped with injector (split modus) at 150° C., FID at 280° C. and a DB-624 column with 0.53 mm I.D. and 3 μm thickness of stationary phase). The oven temperature of the headspace sampler is maintained at 100° C. and the vials are equilibrated for 20 min at 120° C. prior to analyzing the gas phase. The vial pressure is 80 kPa and the flow rate of the mobile phase (helium) is 20 ml/min. GC-temperature program is from 40° C. (1 min), raising with 10° C./min to 240° C. and held for 3 minutes at 240° C. Carrier gas is helium at a pressure of 25 kPa.

The chromatogram of each sample is shown in the overlay plot of FIG. 1. The results in FIG. 1 clearly show that ionic liquids may be used in place of conventional solvents in headspace gas chromatography. Advantageously the ionic liquids due to their high temperature stability allow for an expanded application range that includes the actual conventional solvent peaks.

Example 2

Detection Limit for Solvents (e.g. tetrahydrofuran, THF) in Drug Substance

Two vials are prepared which each contain appr. 100 mg of drug substance, which is dissolved in 1 ml 1-butyl-3-methylimidazolium methane sulfonate or in the conventional solvent dimethylsulfoxide (DMSO).

The chromatograms are obtained using Agilent Equipment (Headspace Autosampler 7694, a Gas chromatograph 5890 equipped with injector (split modus) at 150° C., FID at 280° C. and a DB-624 column with 0.53 mm I.D. and 3 μm thickness of stationary phase). The oven temperature of the headspace sampler is maintained at 100° C. and the vials are equilibrated for 30 min prior to analyzing the gas phase. The vial pressure is 80 kPa and the flow rate of the mobile phase (helium) is 20 ml/min. GC-temperature program is from 40° C. (2 min isothermal), raising with 5° C./min until 125° C., following with 30° C./min to 240° C. and held for 3 minutes at 240° C. isothermal. Carrier gas is helium at a pressure of 32 kPa.

Figure 2:
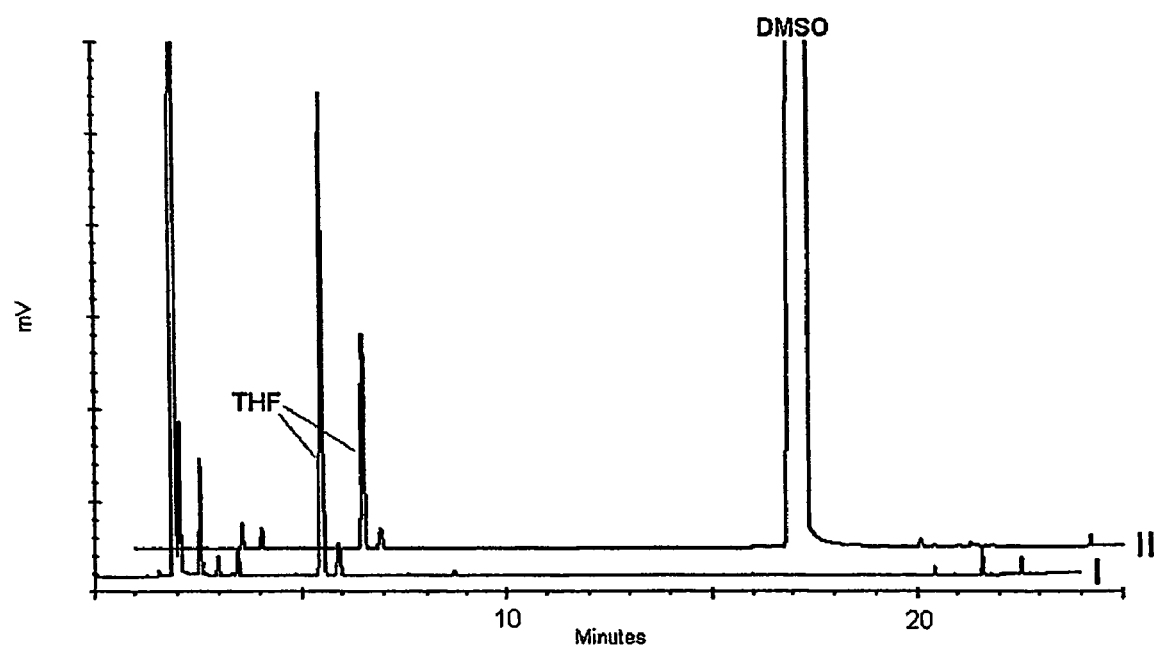
FIG. 2 is a headspace gas chromatogram showing a tetrahydrofuran, THF, containing drug substance dissolved in 1-butyl-3-methyl-imidazolium methane sulfonate (I) and in dimethylsulfoxide (II).

The chromatogram of each sample is shown in the overlay plot of FIG. 2. The results in FIG. 2 clearly show the advantage of using an ionic liquid as a solvent. The detection limit for THF in the drug substance is significantly improved (chromatogram 1).

Example 3

Quantification of High Boiling Compounds

A vial is prepared which contains appr. 23.8 µg dimethyl formamide (DMF), 151.8 µg dimethylsulfoxide (DMSO), 33.2 µg dimethylacetamide (DMA), and 3.9 µg diethyleneglycoldimethylether (DIGLYME), which is dissolved in 1 ml of EMIM bis-(trifluoromethanesulfonyl)-imidate (II). A second vial contains only 1 ml of EMIM bis-(trifluoromethanesulfonyl)-imidate for comparison (I).

The chromatograms are obtained using Agilent Equipment (Headspace Autosampler 7694, a Gas chromatograph 5890 equipped with injector (split modus) at 210° C., FID at 280° C. and a DB-624 column with 0.53 mm I.D. and 3 µm thickness of stationary phase). The oven temperature of the headspace sampler is maintained at 200° C. and the vials are equilibrated for 20 min prior to analyzing the gas phase. The vial pressure is 100 kPa and the flow rate of the mobile phase (helium) is 20 ml/min. GC-temperature program is from 40° C. (2 min isothermal), raising with 8° C./min until 180° C., followed with 15° C./min to 240° C. and hold for 3 minutes at 240° C. isothermal. Carrier gas is helium at a pressure of 32 kPa.

Figure 3:
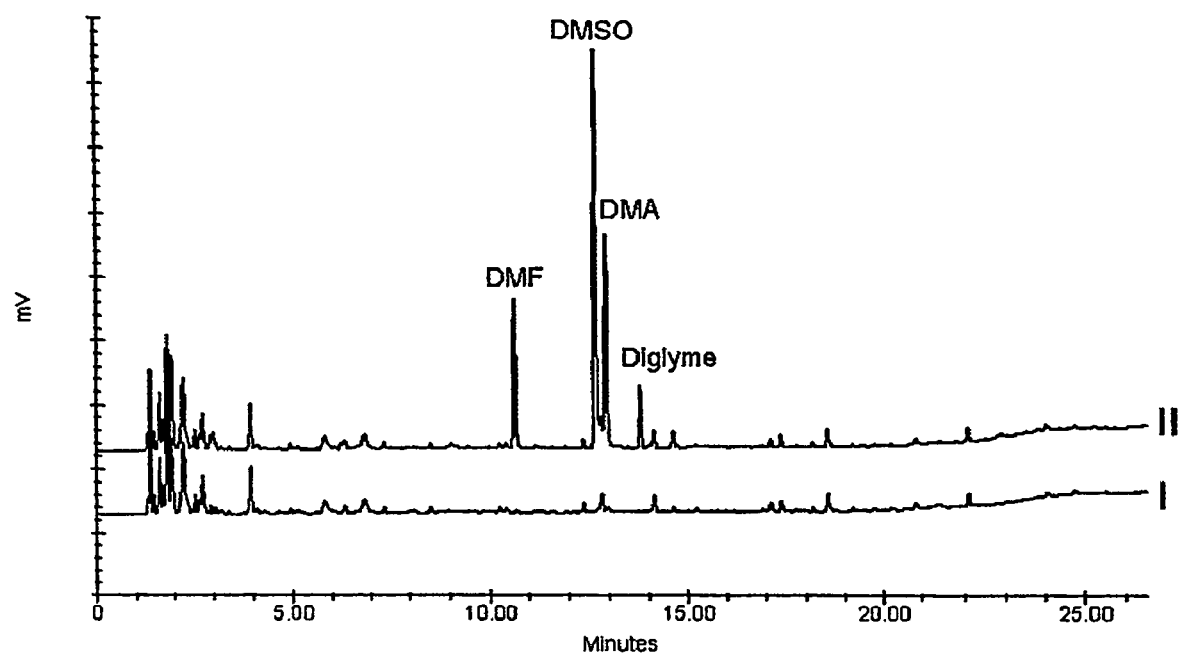
FIG. 3 is a headspace gas chromatogram showing dimethyl formamide (DMF), dimethylsulfoxide (DMSO), dimethylacetamide (DMA) and diethylenegycoldimethylether (DIGLYME) dissolved in 1-ethyl-3-methyl-imidazolium bis-(trifluoromehtanesulfonyl)-imidate (II) and 1-ethyl-3-methyl-imidazolium bis-(trifluoromehtanesulfonyl)-imidate (I).

The chromatogram of each sample is shown in the overlay plot of FIG. 3. The results in FIG. 3 (retention times: appr. 10.5 min for DMF, 12.5 min for DMSO, 13.0 for DMA and 13.5 for DIGLYME). Advantageously high boiling solvents can easily be detected while using an ionic liquid as solvent.

Example 4

Detection of Impurities Co-eluting with Solvents "Hidden Compounds"

Two vials are prepared which each contained appr. 10 mg of drug substance, which is dissolved in 100 µl EMIM bis-(trifluoromethylsulfonyl)-imidate (IL1) or in the conventional solvent dimethylacetamide (DMA).

The chromatograms are obtained using Agilent Equipment (Headspace Autosampler 7694, a Gas chromatograph 5890 equipped with injector (split modus) at 150° C., FID at 280° C. and a DB-624 column with 0.53 mm I.D. and 3 µm thickness of stationary phase). The oven temperature of the headspace sampler is maintained at 150° C. and the vials are equilibrated for 30 min prior to analyzing the gas phase. The vial pressure is 80 kPa and the flow rate of the mobile phase (helium) is 20 ml/min. GC-temperature program is from 40° C. (2 min isothermal), raising with 5° C./min until 125° C., followed with 30° C./min to 240° C. and held for 3 minutes at 240° C. isothermal. Carrier gas is helium at a pressure of 32 kPa.

Figure 4:
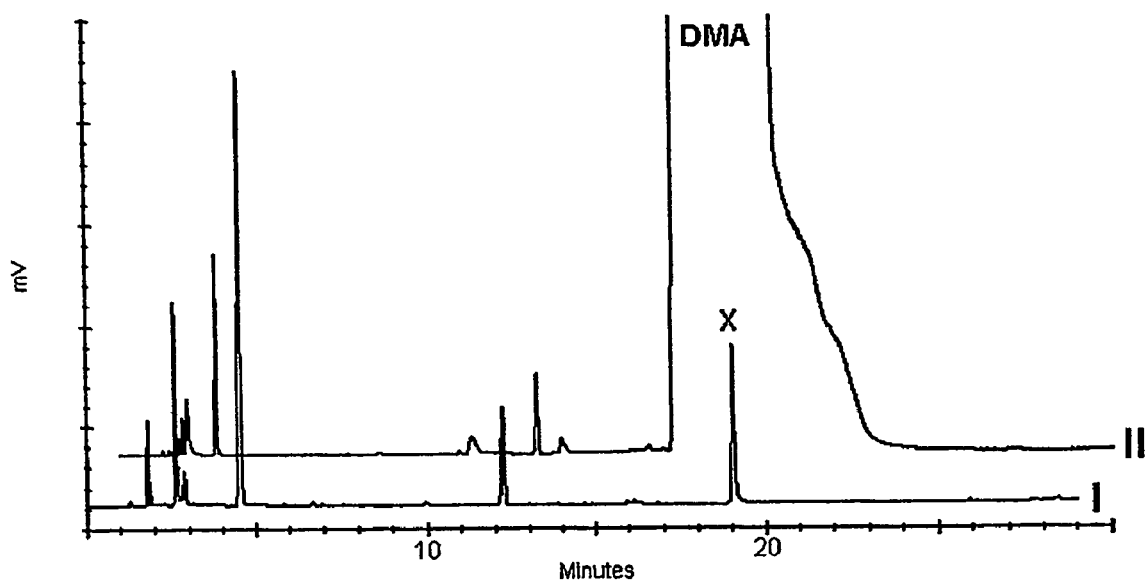
FIG. 4 is a headspace gas chromatogram showing drug substance dissolved in 1-ethyl-3-methyl-imidazolium bis-(trifluoromethylsulfonyl)-imidate (I) and in dimethylacetamide (DMA) (II).

The chromatogram of each sample is shown in the overlay plot of FIG. 4. The results in FIG. 4. clearly show that "hidden compounds" (e.g. peak X) that usually co-elute with classical solvents can now be detected and quantified while using an ionic liquid as new solvent (chromatogram 1).

While the invention has been described with particular reference to certain embodiments thereof, it will be understood that changes and modifications may be made by those of ordinary skill within the scope and spirit of the following claims:

The invention claimed is:

1. A method of performing headspace gas chromatography using ionic liquid as solvents comprising the steps of dissolving or dispersing a sample in at least one ionic liquid, wherein the ionic liquid is a molten salt selected from the group consisting of 1-butyl-3-methylimidazolium hexafluorophosphate, 1-hexyl-3-methylimidazolium hexafluorophosphate, 1-octyl-3-methylimidazolium hexafluorophosphate, 1-decyl-3-methylimidazolium hexafluorophosphate, 1-dodecyl-3-methylimidazolium hexafluorophosphate, 1-ethyl-3-methylimidazolium bis((trifluoromethyl)sulphonyl)amide, 1-hexyl-3-methylimidazolium bis((trifluoromethyl)sulphonyl)amide, 1-hexylpyridinium tetrafluoroborate, 1-octylpyridinium tetrafluoroborate, 1-butyl-3-methylimidazolium tetrafluoroborate, 1-methyl-3-ethyl imidazolium chloride, 1-ethyl-3-butyl imidazolium chloride, 1-methyl-3-butyl imidazolium chloride, 1-methyl-3-butyl imidazolium bromide, 1-methyl-3-propyl imidazolium chloride, 1-methyl-3-hexyl imidazolium chloride; 1-methyl-3-octyl imidazolium chloride, 1-methyl-3-decyl imidazolium chloride, 1-methyl-3-dodecyl imidazolium chloride, 1-methyl-3-hexadecyl imidazolium chloride, 1-methyl-3-octadecyl imidazolium chloride, 1-methyl-3-octadecyl imidazolium chloride; ethyl pyridinium bromide, ethyl pyridinium chloride, ethylene pyridinium dibromide, ethylene pyridinium dichloride, butyl pyridinium chloride, benzyl pyridinium bromide, and mixtures thereof, and volatilizing the volatile components of the sample by headspace gas chromatography.

2. The method according to claim 1 wherein the ionic liquid is selected from the group consisting of 1-octyl-3-methyl-imidazolium hexafluorophosphate, 1-hexyl-3-methy-imidazolium hexafluorophosphate, 1-butyl-3-methyl-imidazolium hexafluorophosphate, 1-butyl-3-methyl-imidazolium tetrafluoroborate, 1-butyl-3-methyl-imidazolium trifluoromethanesulfonate, 1-ethyl-3-methyl-imidazolium trifluoromethanesulfonate, and 1-ethyl-3-methyl-imidazolium bis-(trifluoromethanesulfonyl)-amide.

3. A method of performing headspace gas chromatography using ionic liquid as solvents comprising the steps of dissolving or dispersing a sample in at least one ionic liquid, wherein the ionic liquid is a molten salt selected from the group consisting of an imidazolium salt having formula (I)

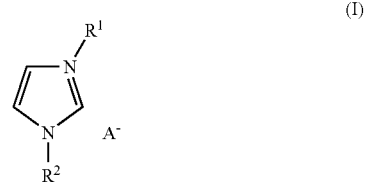

(I)

wherein $R^1$ and $R^2$ are independently selected from the group consisting of a $C_1$-$C_{18}$ aliphatic group and a $C_4$-$C_{18}$ aromatic group, and $A^-$ is an anion; an ammonium salt having formula (II)

(II)

wherein $R^3$, $R^4$, $R^5$ and $R^6$ are independently selected from the group consisting of a $C_1$-$C_{18}$ aliphatic group and a $C_4$-$C_{18}$ aromatic group, and A⁻ is an anion; a phosphonium salt having formula (III)

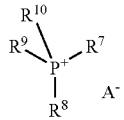

(III)

wherein $R^7$, $R^8$, $R^9$, and $R^{10}$ are independently selected from the group consisting of a $C_1$-$C_{18}$ aliphatic group and a $C_4C_{18}$ a aromatic group, and A⁻ is an anion; a pyridinium salt having formula (IV)

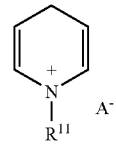

(IV)

wherein $R^{11}$ is selected from the group consisting of a $C_1$-$C_{18}$ aliphatic group and a $C_4$-$C_{18}$ aromatic group, and A⁻ is an anion; and mixtures thereof.

* * * * *